United States Patent [19]

Wiestmiller

[11] Patent Number: 4,478,332
[45] Date of Patent: Oct. 23, 1984

[54] SPONGE ARRAYING AND DISPOSAL RECEPTACLE

[75] Inventor: K. Joyce Wiestmiller, Cobb County, Ga.

[73] Assignee: M.D. Industries, Inc., Northbrook, Ill.

[21] Appl. No.: 355,348

[22] Filed: Mar. 8, 1982

Related U.S. Application Data

[63] Continuation of Ser. No. 195,406, Oct. 9, 1980.

[51] Int. Cl.³ .............................................. B65D 83/10
[52] U.S. Cl. ..................................... 206/361; 206/363; 206/370; 141/83; 141/114; 383/12; 383/33
[58] Field of Search ................... 383/12, 33, 22, 34; 141/83, 10, 68, 114, 313–317; 206/370, 361, 363

[56] References Cited

U.S. PATENT DOCUMENTS

| | | | |
|---|---|---|---|
| 593,346 | 11/1897 | Baehn | 383/22 |
| 2,695,150 | 11/1954 | Criswell | 383/22 |
| 2,740,445 | 4/1956 | Fornell | 383/22 |
| 2,750,091 | 6/1956 | Mattimoe et al. | 141/83 |
| 2,873,905 | 2/1959 | Denton | 383/22 |
| 3,388,882 | 6/1968 | Burroughs et al. | 383/34 |
| 3,425,618 | 2/1969 | Cohen | 383/22 |
| 3,589,595 | 6/1971 | White | 383/33 |
| 4,182,386 | 1/1980 | Alack | 141/83 |

FOREIGN PATENT DOCUMENTS

598069 11/1977 Switzerland ..................... 383/22

*Primary Examiner*—Joseph M. Moy
*Attorney, Agent, or Firm*—Louis Bernat

[57] ABSTRACT

A disposable receptacle for organizing and handling sponges contaminated during surgical procedures. The receptacle comprises a transparent bag and a pair of slightly inclined chutes from which a plurality of prongs extend generally upward. Projections which extend downwardly from the chutes are rigidly attached to inside portions of the bag so that it may be suspended between the chutes for visual observation of its contents. Each of the chutes is detachably mountable on one of the arms of a U-shaped bracket which projects horizontally from a display board. For counting purposes, only one soiled sponge is hung from each prong. Moreover, only an end portion of each soiled sponge is snagged on the prong so that the bulk of the sponge extends over the edge of the chute and downwardly into the bag. Once the prongs have been filled with sponges, the chutes are rotated into the bag. A closure tie for sealing the filled receptacle is attached to the outside of the bag. A slot formed in the tie allows an operator to hang the filled receptacle from one of several sequentially numbered hooks mounted on the display board to allow rapid visual inspection and counting of the soiled sponges throughout the progress of a surgical procedure.

13 Claims, 7 Drawing Figures

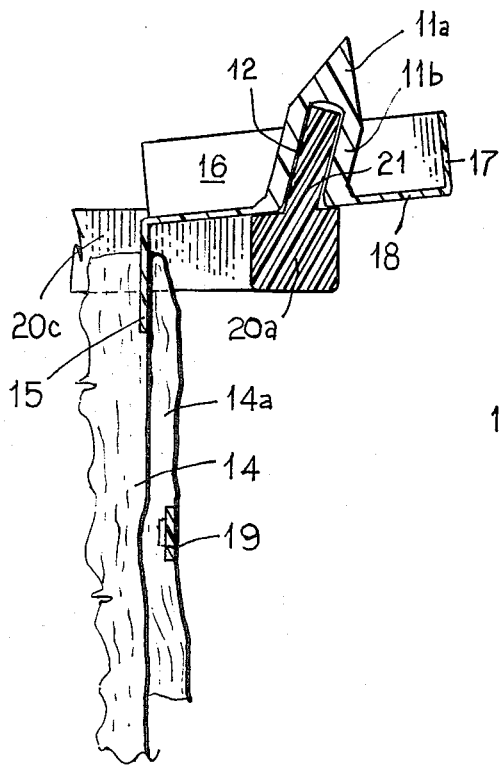
Fig. 3.
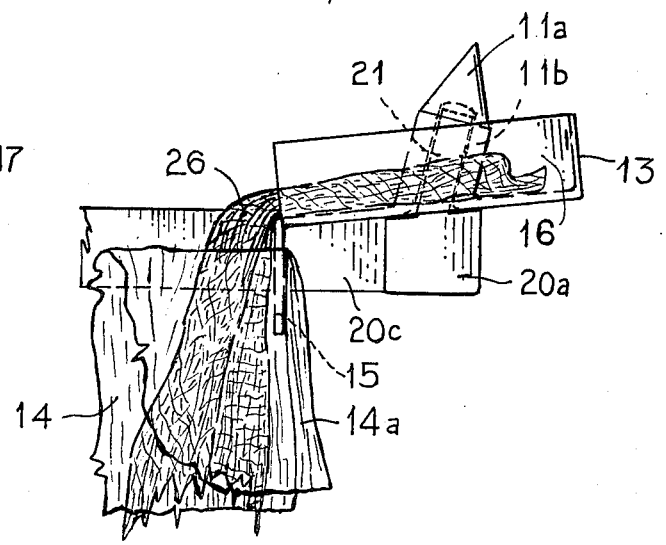
Fig. 5.
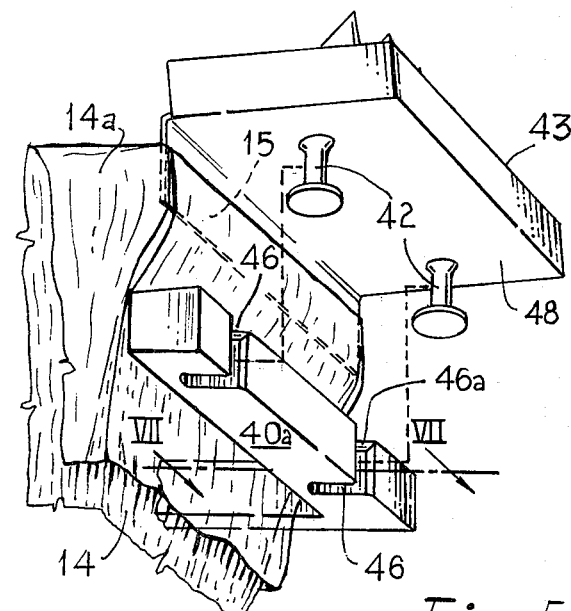
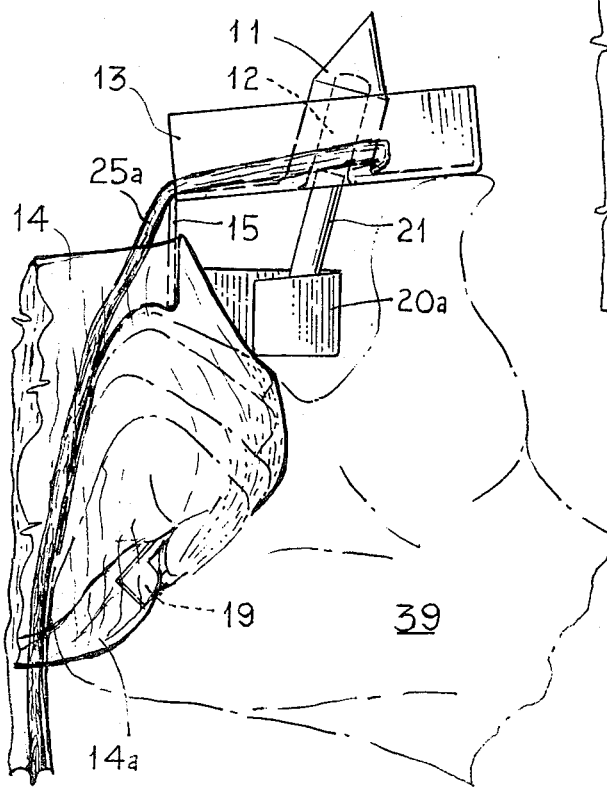
Fig. 4.
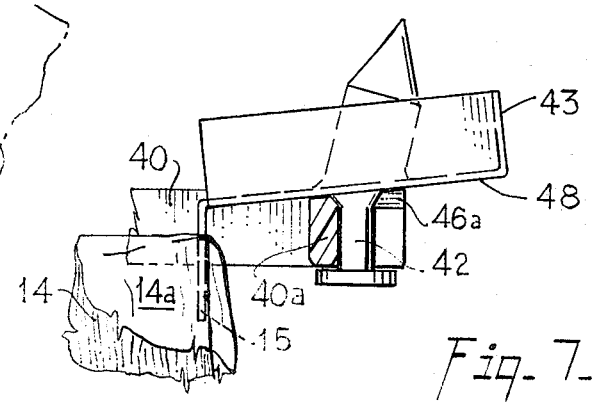
Fig. 7.

SPONGE ARRAYING AND DISPOSAL RECEPTACLE

This is a continuation of application Ser. No. 195,406, filed Oct. 9, 1980.

BACKGROUND OF THE INVENTION

1. Field of the Invention

This invention relates to medical devices and more particularly to a disposable device which facilitates the visual inspection and location of soiled sponges after such have been used to absorb blood and wetting agents during the course of a surgical procedure.

2. Description of the Prior Art

During the performance of surgery, it is common practice to use various size sponges to absorb blood and to moisten exposed organs with saline solution. The soiled sponges must be handled and displayed so that the amount of blood loss can be readily ascertained by visual inspection of those soiled sponges which were used to absorb blood during the operation. Moreover, each and every sponge must be collected and accurately counted to minimize the risk of leaving one of them inside the operative wound. Up to the present time, the methods and devices used or proposed for use for accomplishing these tasks are far from satisfactory.

The prior art discloses disposable devices having individual sites to which soiled surgical sponges can be attached as well as disposable apparatus having individual sites into which such sponges can be inserted for counting purposes. In U.S. Pat. No. 3,613,889, stackable plastic disposable trays having clusters of slits formed therein are provided. A portion of each soiled sponge is pushed through a cluster of slits to secure the sponge to the upper surface of a tray. Unless the sponge is first rolled into a ball, it can easily obscure a cluster of slits to which no sponge has been attached leading to a miscount or, alternately, slide over the sides of the stacked trays causing spillage of fluids to the surrounding environment. More importantly, the soiled sponges which are attached to the stacked trays are not promptly placed in a bag and sealed but rather remain exposed to the atmosphere of the operating room for long periods of time. Only after the final sponge count has been made is a bag pulled over the trays and sealed for disposal. The lengthy exposure of the soiled sponges may cause bacterial contamination of the atmosphere which is highly undesirable.

In U.S. Pat. No. 4,190,153, trays having clusters of slits formed therein are provided which facilitate a more rapid removal of soiled sponges from direct contact with the atmosphere. But each sponge must be pushed individually through a cluster of slits into a cup. Having a cup for each sponge, these trays are impractical for use in an operating room because they would occupy a large area of the sterile field on which space is already at a premium.

A bag strip having individual pockets, each of which can accomodate one soiled sponge, is disclosed in U.S. Pat. No. 3,749,237. A major advantage as well as drawback to the use of the bag strips is their suspendability from any convenient support. Suspension of the bag strips from a support near the operating room table, usually an intravenous bottle standard, provides for ready visual observation of the blood content of the pocketted sponges. But, at the same time, because of the minimum height at which the cross arms of such standards must be placed, the bag strips which depend therefrom are elevated above the patient's incision. As a consequence, soiled sponges, which initially are tossed into an operating room bucket or onto the floor, contaminate the atmosphere in close proximity to the patient each time one of them is lifted to a bag strip pocket for insertion therein. Further, the filled pockets are not sealable which requires extra handling, with virtually no means of preventing blood spillage, prior to the disposal of the bag strips.

Another disposable device to facilitate the counting of sponges is a plastic rim with indentations formed therein for holding the sponges. The rim is supported by an operating room bucket lined with a collection bag. Even when two such devices are utilized, extreme difficulty is experienced by the sponge nurse in maintaining a separation of the sponges used into large and small sizes. Moreover, ready visual inspection of the blood content of the soiled sponges is impractical.

SUMMARY OF THE INVENTION

The object of this invention is to provide an improved method and apparatus for handling soiled surgical sponges. According to the invention, the end portions of a small group of soiled sponges, usually ten in number, are secured serially to a plurality of prongs which are part of a disposable receptacle. To segregate the sponges on the basis of size, at least two essentially identical receptacles are provided. As the end portion of each sponge is secured to a prong, the bulk of each sponge is deposited within the confines of a transparent plastic bag. The bag, together with a pair of chutes from which the prongs extend generally upwardly, comprises the receptacle; the bag is rigidly attached to, and suspendable from, the rear wall of a projection which extends downwardly from each of the chutes. When each of the prongs in a receptacle has one sponge suspended therefrom, the chutes are disengaged from their supports and rotated into the open mouth of the bag. The bag is then promptly sealed for disposal and hung from a sequentially numbered site until the final sponge count is complete.

The chutes of each receptacle are detachably mounted on pegs which extend generally upwardly from the arms of a U-shaped bracket. A display board supporting a pair of brackets is provided so that two receptacles can be mounted side-by-side to facilitate separation of the sponges into large and small sizes. The tips of the prongs connected to each of the detachably-mounted chutes are substantially disposed within a small area of the same horizontal plane. As a consequence, the maximum height to which a sponge must be elevated in order to secure it to a prong need not be a height above the patient's incision. At the same time, the receptacles which are being filled with sponges are at a sufficient height to allow the contents of each bag to be visually inspected. Moreover, the choice of prongs as the means for suspending the sponges allows the receptacles being filled with sponges to occupy a smaller horizontal area of the operating room than if clusters of slits were used.

As an alternative, the means for detachably mounting the chutes of each receptacle comprises at least two pins which extend generally downwardly from the bottom wall of each chute and which are rigidly connected thereto. Each pin is insertable into a slot which is one of a pair of slots formed in each of the arms of a U-shaped bracket.

The method and apparatus for handling solid surgical sponges according to this invention reduces contamination of the operating room atmosphere without employing a time-consuming approach in which each sponge must be packaged individually and yet allows ready visual inspection of the contents of the receptacles being filled. Moreover, blood spillage, once a receptacle is filled with sponges, is virtually eliminated. Even fluids dripping from the uppermost portion of a sponge are captured by the chutes and directed downwardly along the inclined bottom wall thereof into the bag. Since the bag and the chutes are sufficiently inexpensive to be considered disposable, they and the sponges are discarded without direct handling once the sponges have been transferred to a receptacle. Finally, since the bag has negligible weight and can be weighed by resting it on a spring scale at the same time the chutes are detachably mounted on one of the U-shaped brackets, the invention affords a simple, clean technique for computing blood loss from the weight of the blood soaked sponges used in the course of the operation.

BRIEF DESCRIPTION OF THE DRAWINGS

Further details are explained below with the help of the examples illustrated in the attached drawings in which:

FIG. 3 is a cross-section III—III from FIG. 2 on a still further enlarged scale;

FIG. 4 is a frontal elevational view of a fragmentary portion of the receptacle according to FIG. 1 and of a section of the U-shaped bracket showing the simultaneous disengagement of the chute from the bracket and the holding of the cuff of the bag with the use of a single gloved hand;

FIG. 5 is a frontal elevational view of a fragmentary section of the receptacle according to FIG. 1 showing the end portion of a small sponge snagged on one of the prongs of the chute;

FIG. 6 is an exploded view showing in perspective a modified chute to which is attached a fragmentary section of the transparent bag and showing a section of the modified U-shaped bracket; and FIG. 7 is a frontal elevational view of the modified chute to which is attached a fragmentary section of the transparent bag and a cross-section VII—VII from FIG. 6 on an enlarged scale of the modified U-shaped bracket.

Like reference characters indicated corresponding parts throughout the several views of the drawings.

DESCRIPTION OF THE PREFERRED EMBODIMENT

Figure 1:
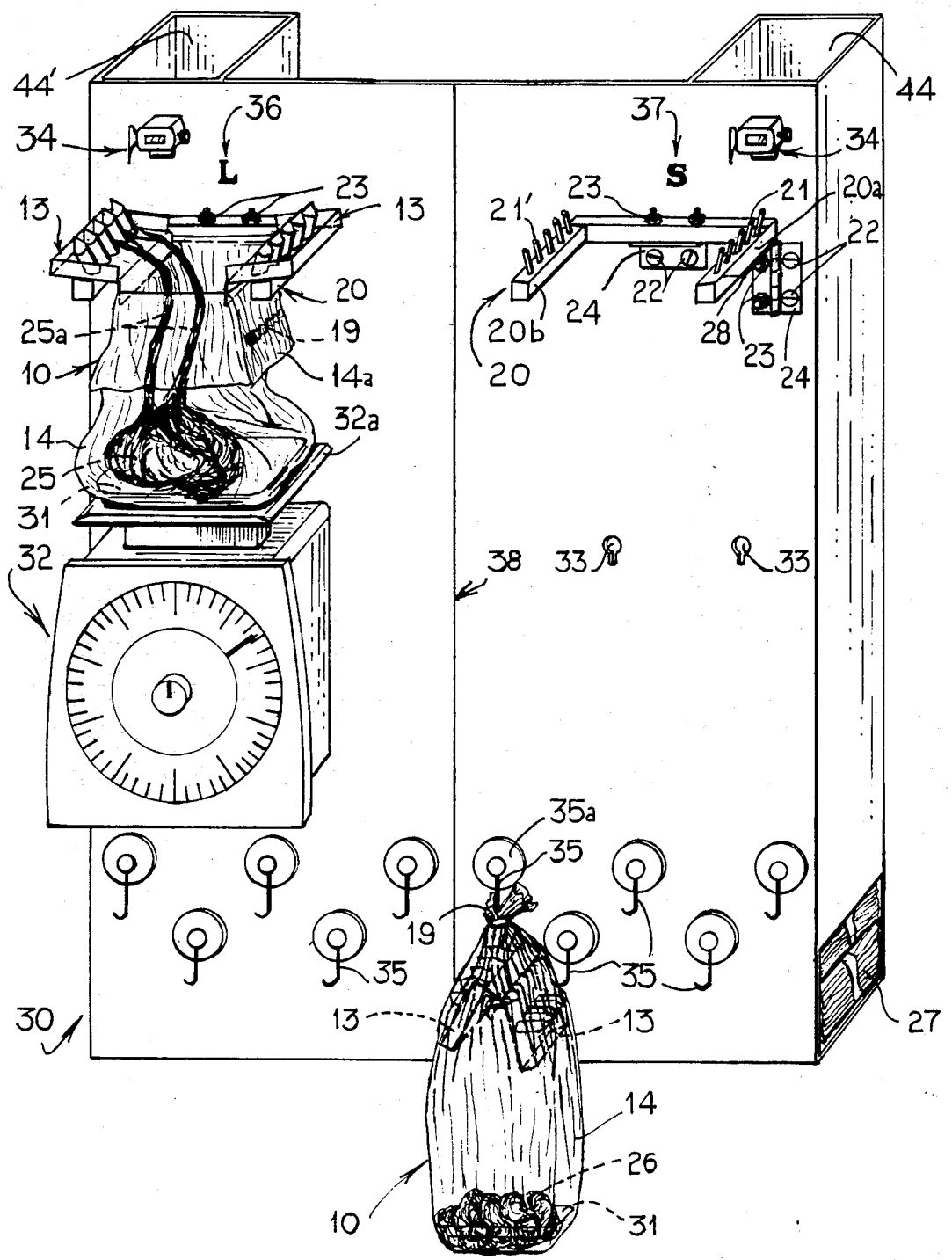
FIG. 1 is a perspective view of an apparatus having a pair of disposable receptacles according to the present invention suspended therefrom, a receptacle which is partially filled with sponges being detachably mounted on a U-shaped bracket and a receptacle which is filled with sponges hanging from a hook.
Figure 2:
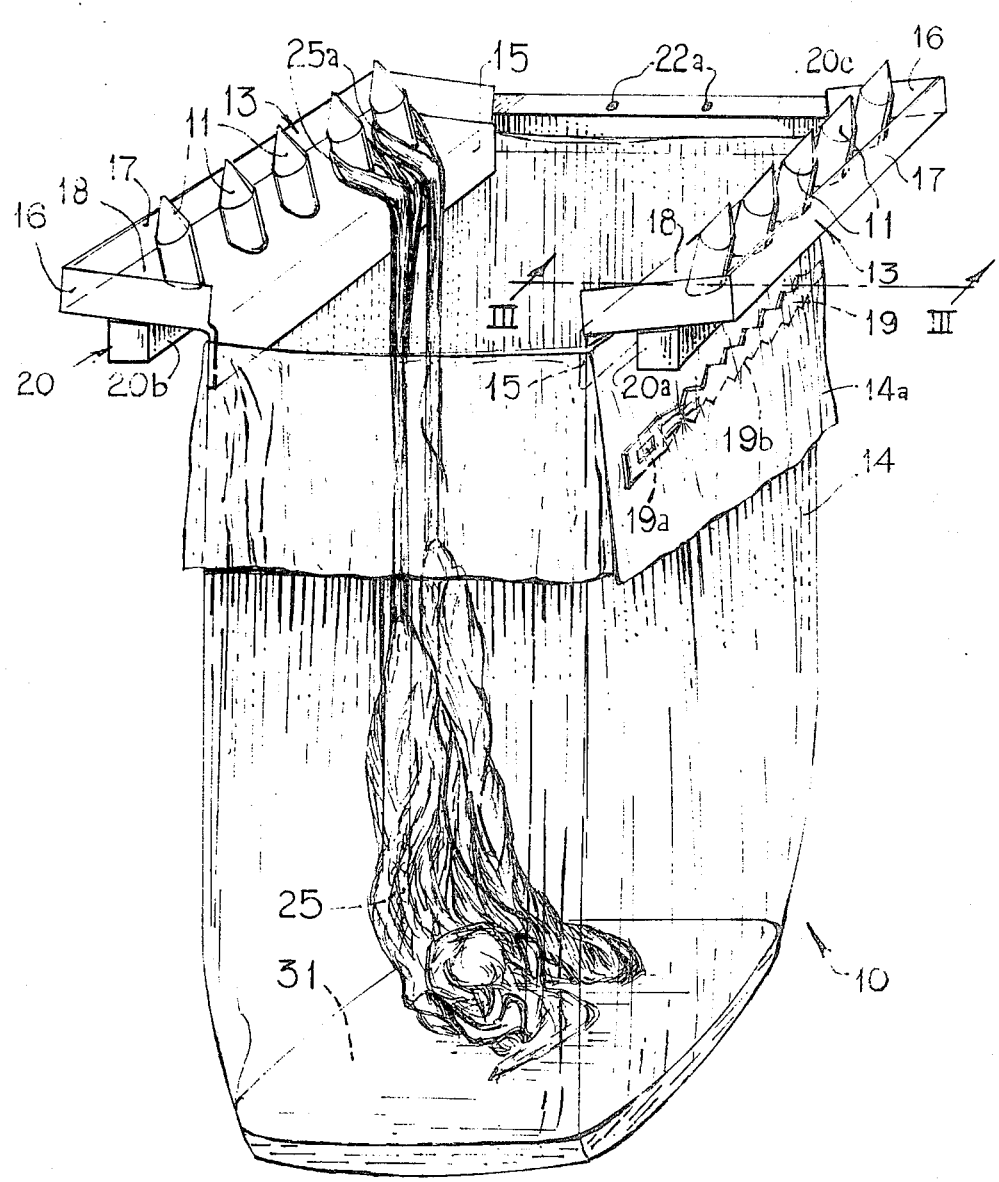
FIG. 2 is an enlarged perspective view of the receptacle according to FIG. 1 with the transparent bag freely suspended between the arms of the U-shaped bracket.

Referring to FIGS. 1 and 2 of the drawings, a disposable receptacle 10 is shown detachably mounted on a U-shaped bracket 20. In the receptacle 10, there is provided a transparent plastic bag 14 formed from polyethylene film or a similar thin plastic material and a pair of chutes 13 formed of a rigid plastic material such as vinyl or the like. Each chute has a slightly inclined wall 18, side and rear walls 16 and 17 which extend upwardly at approximately right angles thereto, and a projection 15 which extends generally downwardly from the front edge of the wall 18. A rear surface of each projection 15 is rigidly attached to an inside surface of the bag 14 either by heat sealing or by an adhesive. A plurality of prongs 11 which are connected to the inclined wall 18 comprise a means for suspending a plurality of sponges in an array. It is envisioned that normally each receptacle 10 will include ten in the number of prongs 11, but it is within the scope of this invention that any number of prongs 11 could be employed. Receptacles having ten or fewer prongs are preferred since arraying small groups of soiled sponges in each receptacle reduces the average length of their exposure to the atmosphere of the operating room prior to their being sealed for disposal.

The prongs 11 and each chute 13 preferably comprise a single, unitary piece formed of plastic in a single injection molding operation. Each prong 11 has a smooth outer surface to facilitate the attachment of a sponge. The smooth surface also allows the sponge to slide from the prong 11 downwardly into the bag 14 when the chute 13 is rotated into the open mouth thereof.

The barrel 11b of each prong 11 is enlarged to form a hollow portion 12. The hollow portion 13 extends through the wall 18 of the chute 13 and is slideable onto one of the pegs 21, 21' as described hereinbelow. A pair of chutes 13 in which each of the prongs 11 has a hollow portion 12 comprises a means for detachably mounting the chutes 13 with a bag 14 suspended in an open position therebetween (see FIGS. 2 through 4).

The joint between the barrel 11b of each prong 11 and the wall 18 is sealed so that no fluids from the sponges can flow downwardly along the pegs 21, 21'. Rather the excess blood and other fluids are contained by the walls 16, 17, and 18 and tend to seep over the front edge of the slightly inclined chute 13 and downwardly through the sponges to accumulate at the base of the bag 14. It is to be noted that there is a small amount of liquid 31 located within the bag 14 which has been drained from the sponges (see FIGS. 1 and 2). Even when the chutes 13 are disengaged from the bracket 20 and folded into the open mouth of the bag 14 as described hereinbelow, all liquid from the sponges is retained within the receptacle 10. The receptacle 10 thus facilitates the handling of the soiled sponges without any spillage of the liquid absorbed by a sponge from the moment the sponge nurse secures it to a chute 13 until its ultimate disposal.

The prongs 11 extend generally upwardly in a direction away from the front edge of the chute 13 to facilitate the retention of the sponges which have been snagged on the prongs. It is not critical that the prongs 11 have pointed tips, however, except when they are used to snap the loopless small sponges. The large sponges which are gauze pads measuring, by way of example, approximately 18 inches by 18 inches are secured to the prongs 11 by slipping a loop 25a sewn to each sponge 25 over the tip 11a of a prong 11 and downwardly onto the barrel 11b (see FIGS. 2 and 3). The loosely-woven fabric of the small sponges 26, on the other hand, is itself impaled on the tips 11a (see FIG. 5). The small sponges are typically bands of gauze which measure approximately 4 inches by 16 inches. The tips 11a which are used for snagging the fabric of the small sponges are pointed with the diameter of the base of a tip 11a being substantially equal to the length thereof.

Alternately, the tips may be formed by pinching the upper end of the barrel 11b together to form a point which is disposed to one side of the prong rather than being centrally located.

As is best seen in FIGS. 1, 2, and 5, the small sponges 26 tend to drape themselves over the front edges of the chutes 13 and to hang downwardly into the bag 14; a substantial portion of each of the larger sponges 25, on the other hand, rests on the bottom of the bag when it is suspended. For both sizes, the bulk of each sponge extends over the front edge of the chute 13 and is disposed within the bag 14. With only a loop or other end portion of sponge draped across the chute 13, overlap between the sponges is minimized. The chance of one or more sponges obscuring a site in the array to which no sponge is attached, leading to a miscount, is virtually nonexistent. Moreover, the retention of only a small portion of each sponge outside of the confines of the bag 14 for counting purposes reduces the amount of surface area of a sponge which is exposed to the circulating air of the operating room. Further, the sponges 25, 26 hanging from the prongs 11 in a transparent bag 14 are totally visible for blood loss estimation at a glance (see FIGS. 1 and 2).

A closure tie 19 attached to the outside surface of the bag 14 on the cuff 14a is used to seal the receptacle 10 once it has been filled with sponges and the chutes 13 folded therein as described hereinbelow. The tie 19 which is attached to the bag 14 by heat sealing is preferably a self-interlocking plastic strip well-known in the art of material handling. The serrated edges 19b catch on the slot 19a to prevent the tie 19 from loosening once it has been formed into a loop and tightened upon an object such as the gathered cuff 14a (see FIG. 1).

The display board 30 which is preferably formed from a sheet of metal comprises a means for exhibiting all of the sponges 25, 26 collected in the course of an operation in an orderly sequence and of containing these sponges within a compact, vertically-elongated region of space. The dimensions of the board 30, by way of example, measure approximately 22 inches in width by 27 inches in height by 6 inches in depth.

A midline 38 is marked on the display board 30 to help the nurse charged with the collection and counting of the sponges differentiate rapidly between the sections set aside for the collection of large and of small sponges. It is recommended that suitable legends 36, 37 such as "LARGE", or, by way of abbreviation, "L", and "SMALL", or "S", be placed on the board 30 to avoid confusion in the placement of the sponges within the appropriate receptacle 10. As illustrated in FIG. 1, recommended positions for these legends 36, 37 on the board 30 are slightly above the U-shaped brackets 20.

A pair of U-shaped brackets 20 which may be formed of a rigid plastic or of metal is mounted on either side of the midline 38. Hinges 24 secure the brackets 20 and angle braces 28 to the board 30 (see FIG. 1). The hinges are attached by any appropriate fasteners such as the nuts 23 and bolts 22. The right angle brace 28 supports one of the outwardly extending arms 20a, 20b of each bracket 20. Each bracket 20 has substantially parallel arms 20a and 20b which have upper surfaces sloped inwardly to support the chutes 13 in slightly inclined positions to facilitate drainage. At least two pegs 21, 21' extend generally upwardly from the arms 20a, 20b. The interval separating each contiguous pair of pegs 21, 21' is a multiple of the interval separating a contiguous pair of prongs 11. By way of example, the latter interval is approximately one inch. In the preferred embodiment illustrated in FIG. 1, five pegs 21, 21' extend upwardly from the arms 20a, 20b. The tips of the pegs 21, 21' of each of the brackets 20 are disposed within substantially the same horizontal plane so that the overall height of the receptacles 10 being filled with sponges above the floor can be minimized and still allow rapid visual inspection of their contents. Further, the horizontal area of the operating room occupied by the pegs 21, 21' and any receptacles 10 mounted thereon is, by way of example, only approximately six by nine inches square. Thus the many sponges which are being counted are arrayed within a restricted height and within a space having a horizontal area which is small in comparison to the dimensions of individual sponges.

In the alternate embodiment illustrated in FIGS. 6 and 7, each chute 43 has at least two pins 42 which extend generally downwardly from the bottom wall 48 thereof. Each pin 42 is insertable into a slot 46 with a chamfer 46a which is one of a pair of slots 46 formed in each of the outwardly extending arms, such as arm 40a, of the U-shaped bracket 40.

As shown in FIG. 1, each of ten hooks 35 are mounted on either side of the midline 38. The base of each hook 35 is embedded in a plastic suction disk 35a attached to the board 30. It is recommended that the numbers "10", "20", "30", "40", and "50" be placed slightly above the hooks 35 in a sequence beginning with the number "10" over the hook situated in the extreme left of each section denoted by the legends 36, 37. In the event each receptacle 10 is filled with less that ten sponges at capacity, an appropriate modified set of sequential numbers is employed.

A pair of sleeves 44 and 44' may be formed at the sides of the board 30 to provide storage for and to dispense packets 27 of sponges. The sleeves 44, 44' also stiffen the display board 30 and provide sites for the attachment of the board 30 to a suitable fixture within the operating room.

The display board 30 is preferably attached to the side of an operating room utility table (not shown) by any suitable fasteners such as screws or magnets. The utility table may be the same table utilized for the preliminary handling of surgical packs and instruments, thereby conserving space in an already crowded operating room. The height of the board 30 above the floor is adjusted so that soiled sponges need not be raised to a height above the patient's incision when they are being deposited within the receptacles 10. The mobility of an operating room utility table facilitates the handling of the soiled sponges. After the surgical packs and instruments have been opened and organized, the utility table can be moved to the area of the sponge collecting buckets. Alternately, the display board 30 may be wall-mounted or attached to a rolling stand.

During the preparations for an operation, each U-shaped bracket 20 is rotated upwardly about the hinges 24 from its shipping position against the face of the board 30 into a horizontal position. The right angle brace 28 is then swung beneath one of the outwardly extending arms 20a, 20b of each bracket 20 to support it. In preparation for collecting the soiled sponges, the number of disposable receptacles 10 which are estimated to be required to be used within the surgical operation are placed within the operating room. A storage bin (not shown) for these receptacles may be attached to the rear face of the board 30 between the sleeves 44, 44'. A receptacle 10 is then mounted on each of the U-shaped brackets 20.

In operations in which computation of blood loss is necessary or desirable, a small balance 32 may be mounted on the board 30 by means of pins (not shown) which engage a pair of apertures 33 formed symmetrically on either side of the midline 38 so that a single balance 32 can be used to weigh collections of either large or small sponges. Alternately, the balance 32 can be secured to the board 30 by spring clips such as those commonly used to secure cabinet doors. As illustrated in FIG. 1, the balance is positioned so that the bag 14 and its contents rest on the platform 32a as the receptacle 10 is being filled with sponges.

The placement of each sponge 25, 26 on a prong 11 is recorded on the appropriate counter 34. It is desirable that an accurate and ongoing count be maintained at all times. The use of dual receptacles and counters facilitates an immediate separation of the sponges by size as they are counted. When all ten of the prongs 11 in a receptacle 10 have been occupied, the pair of chutes 13 is disengaged from the pegs 21, 21'; and the chutes 13 are folded into the bag 14. As illustrated in FIG. 4, the design of the receptacle 10 allows the sponge nurse to grasp the cuff 14a in both hands and in a continuous motion of each hand dislodge each of the chutes 13 and easily fold it into the open mouth of the bag 14. FIG. 4 illustrates the position of the nurse's right hand 39 approximately midway through such a procedure.

The closure tie 19 is used to seal the receptacle 10 once the chutes 13 have been folded into the bag 14. The filled receptacle 10 is then hung from one of the display hooks 35 by passing the end of the tie 19 having the slot 19a over the appropriate hook 35. Once the final sponge count has been made, the filled receptacles 10 are easily removed from the hooks 35 for disposal.

What is claimed is:

1. A receptacle for soiled surgical sponges which comprises: a transparent bag; at least two chutes; a projection which is connected to each chute, each projection being attached to the bag; a means connected to each chute for detachably mounting the chute with the bag suspended in an open position between the chutes; and sponge supporting means comprising a plurality of prongs which extend generally upwardly from each chute and in a direction away from the front edge thereof, said supporting means receiving a plurality of sponges in an array in which each sponge extends over the front edge of one of the chutes and downwardly into the bag, so that only a small portion of each sponge is retained outside of the confines of the open bag while the sponges are being arrayed and counted and the bulk of each of the sponges is readily observable visually for its blood content.

2. A receptacle for soiled surgical sponges according to claim 1 in which the plurality of prongs and the chute from which they extend comprise a single, unitary piece formed of plastic.

3. A receptacle for soiled surgical sponges according to claim 1 wherein the detachable mounting means further comprises at least two of the prongs extending from each chute having a hollow portion which communicates with the bottom surface of the chute, the inner surfaces of each hollow portion being accessible from the outside and being adapted to be slidably mountable on a peg.

4. A receptacle for soiled surgical sponges according to claim 3 wherein the joints between the chutes and each of the prongs are sealed and each chute includes a bottom wall and at least one wall which is disposed generally at right angles thereto and which extends upwardly therefrom, so that fluids dripping from the soiled sponges are retained within the receptacle.

5. A receptacle for soiled surgical sponges according to claim 1 wherein the detachable mounting means further comprises at least two pins which extend generally downwardly from each chute and which are rigidly connected thereto, each pin being adapted to be inserted into a slot formed in one of the arms of a U-shaped bracket.

6. A receptacle for soiled surgical sponges according to claim 1 wherein each chute comprises a bottom wall and the upper surfaces of the prongs connected to each chute define a generally upwardly extending plane which is disposed at an acute angle to the bottom wall of the chute, thereby facilitating the snagging of a soiled sponge on each of the prongs and the filling of the prongs connected to a chute in a serial order.

7. A receptacle for soiled surgical sponges according to claim 1 wherein the tips of the prongs connected to each chute are disposed generally within a small area of a plane which is substantially parallel the bottom wall of the chute so that the maximum height to which a sponge must be elevated to secure it to a prong can be adjusted to a height below the patient's incision.

8. Apparatus to facilitate the handling, counting and disposal of surgical sponges in an operating room comprising: a display board having at least one pair of arms which are extendable substantially perpendicularly to the board; and a receptacle having a transparent bag and at least two chutes, each chute having a projection which is attached to the bag; the chutes having detachable mounting means cooperating with means on the pair of arms for retaining one of the chutes on each of the arms thereof for suspending the bag in an open position between the chutes; and a means connected to each chute for supporting a plurality of sponges in an array in which each sponge extends over the front edge of one of the chutes and downwardly into the bag, so that only a small portion of each sponge is retained outside of the confines of the open bag while the sponges are being arrayed and counted and the bulk of each of the sponges is readily observable visually for its blood content.

9. The apparatus to facilitate the handling, counting and disposal of surgical sponges in an operating room according to claim 8 wherein the detachable mounting means comprises at least two prongs extending from each chute, each prong having a barrel with a hollow portion formed therein, the hollow portion communicating with the bottom surface of the chute, the surfaces of each hollow portion being accessible from the outside; and the chute retaining means comprises at least one pair of pegs which extend generally upwardly from each of the arms, the barrel of each prong being slidably mountable on one of the pegs, the pegs being aligned with an equal number of hollow portions formed in the prongs of the contiguous chute.

10. The apparatus to facilitate the handling, counting and disposal of surgical sponges in an operating room according to claim 8 wherein the detachable mounting means comprises a pair of pins which extend generally downwardly from the bottom wall of each of the chutes and which are connected thereto, and the chute retaining means comprises a pair of slots formed in each of the arms into which the pair of pins are insertable.

11. The apparatus to facilitate the handling, counting and disposal of surgical sponges in an operating room according to claim 8 which further comprises a plurality of sequentially numbered sites, each site having a hook attached thereto, each hook being adapted to support a receptacle so that receptacles which have been filled with soiled surgical sponges and have been sealed for disposal can be exhibited in an orderly sequence within a compact region of space, thereby facilitating a final sponge count.

12. The apparatus to facilitate the handling, counting and disposal of surgical sponges in an operating room according to claim 8 which further comprises a midline marked on the display board, the display board having a pair of arms on either side of the midline, thereby facilitating the separation of soiled surgical sponges by size.

13. The apparatus to facilitate the handling, counting and disposal of surgical sponges in an operating room according to claim 8 wherein the arms are disposed substantially parallel to each other and the upper surface of each arm is sloped downwardly in a direction toward the other arm so that each of the chutes are supported in a slightly inclined position to facilitate the drainage of fluids into the bag.

* * * * *